(12) United States Patent
Cho et al.

(10) Patent No.: US 9,290,542 B2
(45) Date of Patent: Mar. 22, 2016

(54) PHARMACEUTICAL COMPOSITION FOR PREVENTING OR TREATING ARTERIOSCLEROSIS

(71) Applicant: EYEGENE, INC., Seoul (KR)

(72) Inventors: Yang Je Cho, Seoul (KR); Jin Wook Jang, Seoul (KR); Hyeong Joon Lim, Gyeonggi-do (KR)

(73) Assignee: EYEGENE, INC., Seoul (KR)

( * ) Notice: Subject to any disclaimer, the term of this patent is extended or adjusted under 35 U.S.C. 154(b) by 0 days.

(21) Appl. No.: 14/384,646

(22) PCT Filed: Mar. 11, 2013

(86) PCT No.: PCT/KR2013/001944
§ 371 (c)(1),
(2) Date: Sep. 11, 2014

(87) PCT Pub. No.: WO2013/137606
PCT Pub. Date: Sep. 19, 2013

(65) Prior Publication Data
US 2015/0038405 A1    Feb. 5, 2015

(30) Foreign Application Priority Data

Mar. 12, 2012  (KR) ........................ 10-2012-0024903

(51) Int. Cl.
*A61K 38/00* (2006.01)
*A61P 9/10* (2006.01)
*C07K 14/47* (2006.01)
*C07K 14/00* (2006.01)
*A61K 38/17* (2006.01)

(52) U.S. Cl.
CPC ................ *C07K 14/00* (2013.01); *A61K 38/17* (2013.01)

(58) Field of Classification Search
CPC ................................ A61K 38/17; C07K 14/00
See application file for complete search history.

(56) References Cited

U.S. PATENT DOCUMENTS

2009/0220463 A1 * 9/2009 Kim et al. ................... 424/93.7
2010/0150939 A1   6/2010 Blanchetot et al.

FOREIGN PATENT DOCUMENTS

WO    WO2007083949    *  7/2007  ........... C07K 14/435

OTHER PUBLICATIONS

Schaefer et al. Familial Apolipoprotein E Deficiency. J Clin Invest, 1986. vol. 78, pp. 1206-1219.*
International Search Report for PCT/KR2013/001944.
NCBr, Genbank accession No. AAS48597.1 (May 14, 2008) (See amino acid residue 452-509).
Charrier-Hisamuddin et al., "ADAM-15: a metalloprotease that mediates inflammation", The FASEB Journal, vol. 22, pp. 641-653 (2008) (See abstract and pp. 643-644).
Al-Fakhri et al., "Increased expression of disintegrin-metalloproteinases ADAM-15 and ADAM-9 following upregulation of integrins a5b 1 and avb3 in atherosclerosis", Journal of Cellular Biochemistry, vol. 89, pp. 808-823 (2003) (See abstract.).

* cited by examiner

*Primary Examiner* — Marcela M Cordero Garcia

(57) ABSTRACT

The present invention provides a pharmaceutical composition for preventing or treating arteriosclerosis, comprising: a pharmaceutically effective amount of a protein comprising the amino acid sequence of SEQ ID NO: 1; and a pharmaceutically acceptable carrier. The composition of the present invention exhibits no toxicity in the liver or kidney and effectively reduces the formation of atherosclerotic plaques, thereby exhibiting efficacy in treating arteriosclerosis.

2 Claims, 4 Drawing Sheets

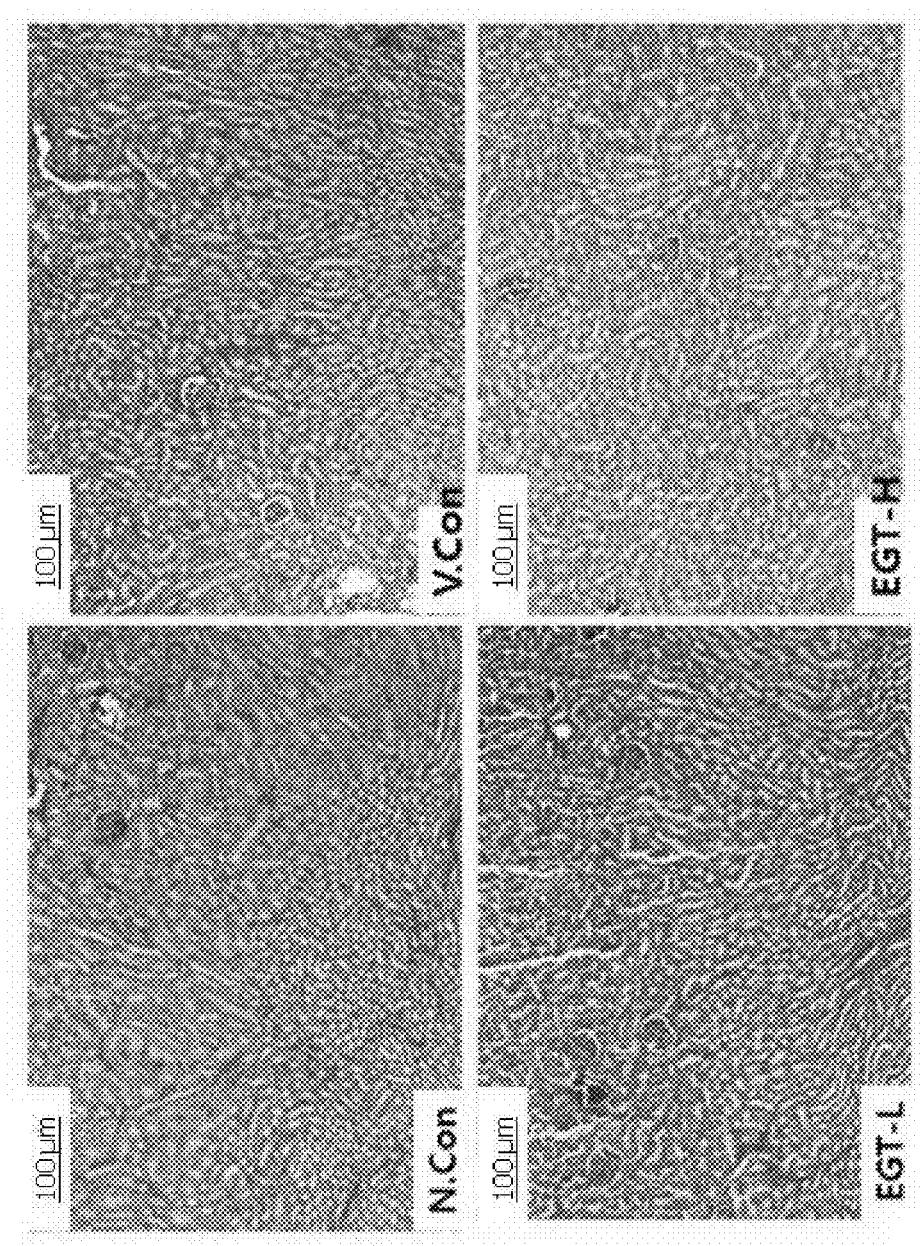

PHARMACEUTICAL COMPOSITION FOR PREVENTING OR TREATING ARTERIOSCLEROSIS

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/001944, filed 11Mar. 2013, which claims priority to Korean Patent Application No. 10-2012-0024903, filed Mar. 12, 2012, entire contents of which are incorporated herein by reference.

BACKGROUND OF THE INVENTION

1. Field of the Invention

The present invention was made with the support of the Ministry of Knowledge Economy, Republic of Korea, under Project No. 10037336. This project was conducted in the project titled "Development on diabetic retinopathy treatment" in the project named "Knowledge economy innovation projects Source industrial technology development" by Eyegene, Inc., under management of the Korea Evaluation Institute of Industrial Technology, during the period of 2010.06.01-2015.03.31.

This application claims the benefit of Korean Patent Application No. 10-2012-0024903, filed Mar. 12, 2012, the entire contents of which are incorporated by reference herein.

The present invention relates to pharmaceutical compositions for preventing or treating arteriosclerosis.

2. Description of the Related Art

With the recent westernization of lifestyle, the incidences of arteriosclerosis diseases such as angina, intermittent claudication, myocardial infarction, and cerebral infarction, are gradually increasing, along with cancers. Once having occurred, these diseases are seriously difficult to treat and remarkably lower the quality of life. Therefore, the countermeasure to control prevention or medical conditions of the diseases is very important from the social view.

Arteriosclerosis is the accumulating of fat on the wall of the blood vessel and thickening of the wall of the blood vessel for a long period of time. Hyperlipidemia, particularly hypercholesteremia, is mainly an important risk factor, and hypertension and diabetes are also known to be risk factors. With the recent westernized diet and aging population, the occurrence of arteriosclerosis and related brain cardiovascular disease are largely increasing. In the progress of atherosclerosis, vascular endothelial cells constituting the inner blood vessel are first damaged due to oxidized lipid, high blood pressure, fast blood flow rate, and the like, and the fat is generally accumulated on the blood vessel, resulting in infiltration of macrophages and T cells and an inflammation response, and thus vascular smooth muscle cells proliferate to thicken the blood vessel. As a result, the blood vessel is narrowed and thus the blood cannot flow smoothly. In the case where the coronary artery of the heart is narrowed, angina pains resulting from an insufficient supply of the blood to the heart caused by immoderate exercise and the like are shown. Meanwhile, in the case where protease generated by macrophages inside the thickened blood vessel (arteriosclerosis plaque) is very active, a part of the tissue which covers the plaque bursts. Here, fat, surrounding protein, and the like contained in the plaque comes out in the blood vessel to form blood clots, which block the coronary artery of the heart, the blood vessel in the brain, and the like, causing myocardial infarction or stroke.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop substances having an effect on the prevention or treatment of arteriosclerosis. As a result, we have discovered that a protein having the amino acid sequence of SEQ ID NO:1 has a treatment effect on arteriosclerosis.

Accordingly, it is an object of this invention to provide a pharmaceutical composition for preventing or treating arteriosclerosis.

It is another object of this invention to provide a method of preventing or treating arteriosclerosis.

Other objects and advantages of the present invention will become apparent from the detailed description to follow taken in conjugation with the appended claims and drawings.

BRIEF DESCRIPTION OF THE DRAWINGS

FIG. 4 illustrates images showing pathological analysis results of the kidney tissue according to administration of a protein consisting of the amino acid sequence of SEQ ID NO: 1 in ApoE-KO mice.

DETAILED DESCRIPTION

Figure 1:
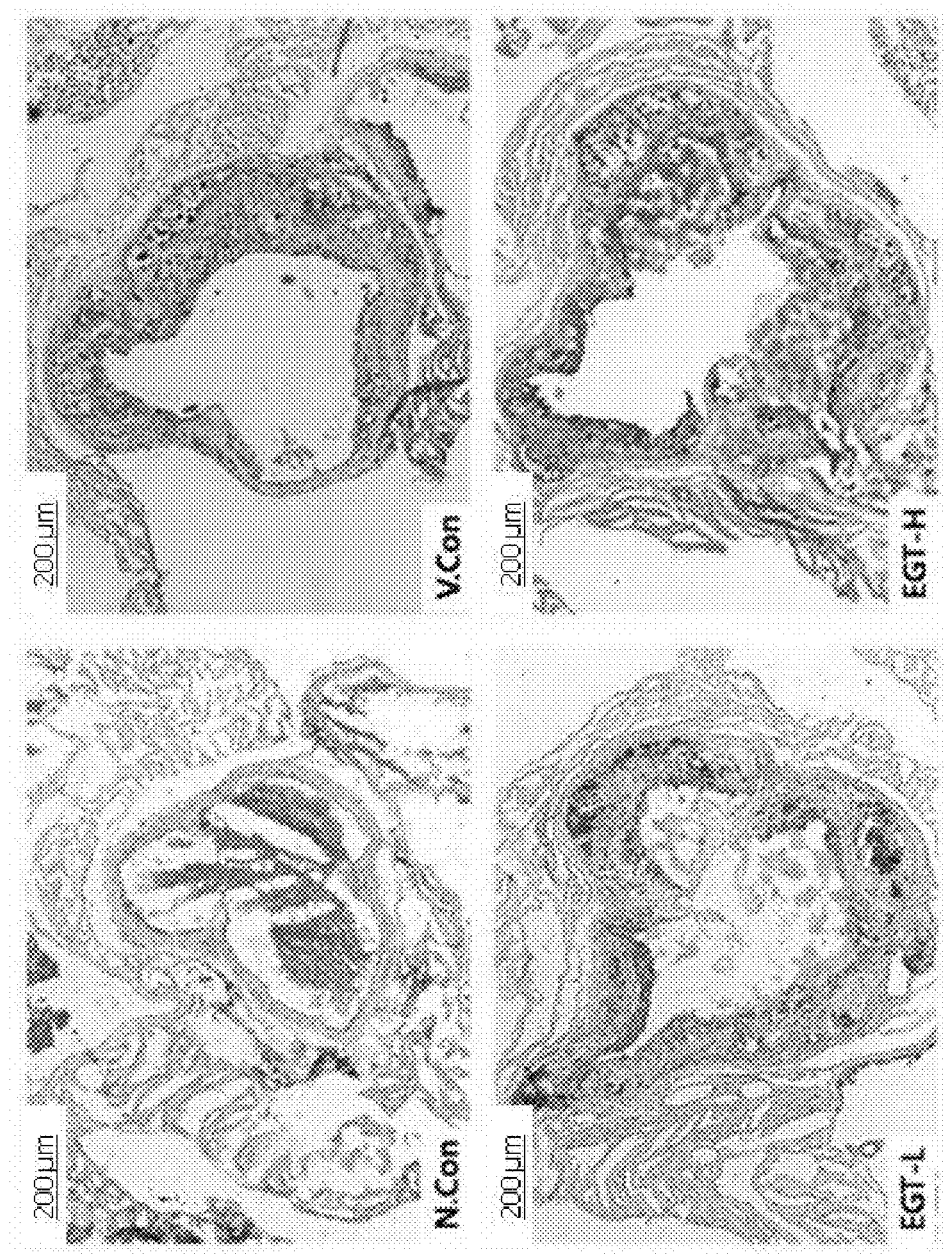
FIG. 1 illustrates images showing pathological analysis results of aortic lesion change according to administration of a protein consisting of the amino acid sequence of SEQ ID NO: 1 in ApoE-KO mice.

In one aspect of the present invention, there is provided a pharmaceutical composition for preventing or treating arteriosclerosis, comprising (a) a pharmaceutically effective amount of a protein consisting of the amino acid sequence of SEQ ID NO:1; and (b) a pharmaceutically acceptable carrier.

In another aspect of this invention, there is provided a method for preventing or treating arteriosclerosis, comprising administering to a subject a composition comprising (a) a pharmaceutically effective amount of a protein consisting of the amino acid sequence of SEQ ID NO:1; and (b) a pharmaceutically acceptable carrier.

The present inventors have made intensive researches to develop substances having an effect on the prevention or treatment of arteriosclerosis. As a result, we have discovered that a protein having the amino acid sequence of SEQ ID NO:1 has a treatment effect on arteriosclerosis.

The pharmaceutical composition of the present invention includes a protein consisting of the amino acid sequence of SEQ ID NO: 1 as an active ingredient. The protein of the present invention exhibits stability in itself, but can improve the stability more and more by modifying amino acid residues. For example, an acetyl group, a fluorenyl methoxy carbonyl group, a formyl group, a palmitoyl group, a myristyl group, a stearyl group, or a polyethylene glycol (PEG) protection group is bound to at least one amino acid of the amino acid sequence of SEQ ID NO: 1.

It is obvious to those skilled in the art that the protein including the amino acid sequence of SEQ ID NO: 1 used in the present invention is not limited to amino acid sequences described in the sequence listing of the present invention within the range of capability to treat atherosclerosis.

For example, a variant may be obtained that exhibits almost the same activity as the protein of the amino acid sequence of SEQ ID NO: 1 even when the variant causes a change in the amino acid sequence of SEQ ID NO: 1.

It is obvious to those skilled in the art that the biological function equivalent that can be included in the protein used in the present invention is limited to a variant of the amino acid sequence exhibiting the equivalent biological activity to the protein of the amino acid sequence of SEQ ID NO: 1.

Such amino acid variations may be provided on the basis of a relative similarity of amino acid side chains, e.g., hydrophobicity, hydrophilicity, charge and size. By the analysis for size, shape and type of the amino acid side chains, it could be clear that all of arginine, lysine and histidine residues are those having positive charge; alanine, glycine and serine have a similar size; phenylalanine, tryptophan and tylosin have a similar shape. Accordingly, based on these considerable factors, arginine, lysine and histidine; alanine, glysine and serine; and phenylalanine, tryptophane and tylosin may be considered to be biologically functional equivalents.

For introducing mutation, a hydropathic index of amino acids may be considered. Based on the hydrophobicity and the charge, the hydropathic index is given to each amino acid: isoleucine (+4.5);

valine (+4.2); leucine (+3.8); phenylalanine (+2.8); cysteine (+2.5); methionine (+1.9); alanine (+1.8); glysine (−0.4); threonine (−0.7); serine (−0.8); tryptophane (−0.9); tylosin (−1.3); proline (−1.6); histidine (−3.2); glutamate (−3.5); glutamine (−3.5); aspartate (−3.5); asparagin (−3.5); lysine (−3.9); and arginine (−4.5).

For providing an interactive biological function of proteins, the hydropathic index of the amino acid is very important. It is well known to one of skill in the art that variations can possess a similar biological activity only where proteins are replaced with amino acids having similar hydropathic index. Where variations are intended to introduce based on the hydropathic index, the substitution is preferably performed between amino acid residues having no more than ±2 difference in hydropathic index values more preferably within ±1, much more preferably within ±0.5.

It would be also obvious to those of skill in the art that substitutions of amino acids with other amino acids having similar hydrophilicity values may result in the generation of variants having biologically equivalent activities. As disclosed in U.S. Pat. No. 4,554,101, each amino acid residue is assigned the following hydrophilicity values: arginine (+3.0); lysine (+3.0); aspartate (+3.0±1); glutamate (+3.0±1); serine (+0.3); asparagin (+0.2); glutamine (+0.2); glysine (0); threonine (−0.4); proline (−0.5±1); alanine (−0.5); histidine (−0.5); cysteine (−1.0); methionine (−1.3); valine (−1.5); leucine (−1.8); isoleucine (−1.8); tylosin (−2.3); phenylalanine (−2.5); tryptophane (−3.4).

Where variations are intended to introduce based on the hydrophilicity index, the substitution is preferably performed between amino acid residues having no more than ±2 difference in hydrophilicity index values more preferably within ±1, much more preferably within ±0.5.

The alteration of amino acid residues not to substantially impair protein activity is well known to one skilled in the art (H. Neurath, R. L. Hill, The Proteins, Academic Press, New York, 1979).

Such amino acid alteration includes Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, but not limited to.

Considering the afore-mentioned variations having biologically equivalent activities, it could be understood that the protein having the amino acid sequence of SEQ ID NO:1 includes substantially identical sequences to the sequences set forth in the appended Sequence Listing. The substantially identical sequences refers to those showing preferably at least 61%, more preferably at least 70%, still more preferably at least 80%, most preferably at least 90% nucleotide similarity to the sequences of the appended Sequence Listing, as measured using one of the sequence comparison algorithms. Methods of alignment of sequences for comparison are well-known in the art. Various programs and alignment algorithms are described in: Smith and Waterman, *Adv. Appl. Math.* 2:482(1981); Needleman and Wunsch, *J. MoI. Bio.* 48:443 (1970); Pearson and Lipman, *Methods in MoI. Biol.* 24: 307-31(1988); Higgins and Sharp, *Gene* 73:237-44(1988); Higgins and Sharp, *CABIOS* 5: 151-3(1989); Corpet et al., *Nuc. Acids Res.* 16:10881-90(1988); Huang et al., *Comp. Appl. BioSci.* 8:155-65(1992); and Pearson et al., *Meth. MoI. Biol.* 24:307-31(1994). The NCBI Basic Local Alignment Search Tool (BLAST) (Altschul et al., *J. MoI. Biol.* 215: 403-10 (1990)) is available from several sources, including the National Center for Biological Information (NBCI, Bethesda, Md.) and on the Internet, for use in connection with the sequence analysis programs blastp, blasm, blastx, tblastn and tblastx. It can be accessed at http://www.ncbi.nlm.nih-.gov/BLAST/. A description of how to determine sequence identity using this program is available at http://www.ncbi.nlm.nih.gov/BI-AST/blast help.html.

The composition of the present invention has an efficacy to prevent or treat arteriosclerosis.

As used herein, the term "arteriosclerosis" refers to a pathological condition where the elasticity of the arteries decreases, and fat, fibrous tissue, blood clots, and the like are accumulated on the wall of the artery to narrow or block the wall of the blood vessel, and a fatal disease where the arteriosclerosis in the blood vessel in the brain causes stroke, the arteriosclerosis in the heart causes myocardial infarction and angina, and the complete blocking of the artery results in necrosis, that is, the death of portions of the body to which the corresponding artery provides the blood.

According to a preferable embodiment of the present invention, the arteriosclerosis in the present invention is atherosclerosis, medialcalcific sclerosis, or arteriolosclerosis, preferably atherosclerosis or medialcalcific sclerosis, and more preferably atherosclerosis.

According to a preferable embodiment of the present invention, the arteriosclerosis in the present invention occurs in patients with a deficiency in the apolipoprotein E gene.

According to a preferable embodiment of the present invention, the composition of the present invention reduces the formation of atherosclerotic plaque in an arteriosclerosis model. The formation of atherosclerotic plaque is reduced by preferably 10-80%, more preferably 20-70%, and still more preferably 30-60%.

Where the composition of this invention is prepared as a pharmaceutical composition, the pharmaceutical composition of this invention contains a pharmaceutically acceptable carrier. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered via the oral or parenteral, and it is preferably administered via oral.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Preferably, the pharmaceutical composition of the present invention is administered with a daily dose of 0.0001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

The features and advantages of this invention will be summarized as follows:

(i) The present invention provides a pharmaceutical composition for preventing or treating arteriosclerosis containing a protein consisting of the amino acid sequence of SEQ ID NO: 1.

(ii) The composition of the present invention has no toxicity in the liver and the kidney, and reduces the formation of atherosclerotic plaque, thereby exhibiting useful efficacy in treating arteriosclerosis.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
Preparation of Test Material 1 mg/ml of a stock was prepared by completely dissolving a protein powder consisting of the amino acid sequence of SEQ ID NO: 1 in 1 ml of distilled water. In order to prepare 100 µg/kg of a sample, the stock was 50-fold diluted (A) (PBS 4.9 ml+test material stock 0.1 ml added (a total of 5 ml)). After that, the prepared sample was administered at 5 µl per 1 g of mouse weight. In order to prepare 10 µg/kg of a sample, the (A) solution was 10-fold diluted (PBS 4.5 ml +test material 0.5 ml added (a total of 5 ml)). After that, the prepared sample was administered at 5 µl per 1 g of mouse weight.

Animals

Mice (C57BL/6.KOR/Stm Slc-Apoe$^{shl}$) were used in the experiment, and here 36 male mice at 6-week-old (body weight: 20-25 g) were purchased from Central Lab. Animal Inc., and then acclimated for 1 week prior to the experiment. The mice were bred under conditions of a temperature of 22±2° C., humidity of 50±10%, number of times of ventilation of 10-20 times/hour, 12-hour light/dark cycle, and illumination of 150-300 Lux (3 mice per cage). The experiment was conducted in compliance with the provisions of the Animal Protection Act (enacted May 31, 1991, Act No. 4379; amended by Act No. 8852, Feb. 29, 2008).

Test Groups of Animals
Test groups were configured as shown in Table 1.

TABLE 1

| Test groups | | | |
| --- | --- | --- | --- |
| Group | Treatment group | | Mouse number |
| N.Con | PBS | Normal diet | 6 |
| V.Con | PBS | Atherosclerosis- inducing diet | 6 |
| EGT-L | EGT022 10 µg/kg | | 12 |
| EGT-H | EGT022 100 µg/kg | | 12 |

Evaluation by Animal Group

After C57BL/6.KOR/Stm Slc-Apoe$^{shl}$ mice which have been frequently used to evaluate the atherosclerosis model were purchased, the mice were acclimated for 1 week and then randomly divided into a total of four groups. The mice were freely fed a normal rodent diet or an atherosclerosis-inducing diet (Piagen D12336). The body weight was measured once a week, and the blood was collected from the orbital veins once every three weeks. After atherosclerosis was induced by the atherosclerosis-inducing diet for 12 weeks, a protein consisting of the amino acid sequence of SEQ ID NO: 1 was subcutaneously injected to the back of the mouse at 10 µg/kg or 100 µg/kg with 100 µl per dose.

Histopathological Analysis of Atherosclerosis Region

The animals were sacrificed 1 week after the administration of the protein consisting of the amino acid sequence of SEQ ID NO: 1, followed by blood collection, and the heart, and the ascending aorta to the thoracic aorta were incised and then fixed with 10% neutral formalin. The heart was hardened in a 20% sucrose solution, followed by cutting, and then embedded with OCT compound. Then, the aortic arch was sliced into a thickness of 10 µm using cryostat microtome, thereby obtaining slides. In addition, for the evaluation of atherosclerotic plaque formed in the aortic arch, the fat ingredients were stained with Oil Red O to measure the area of the atherosclerotic plaque, thereby confirming whether the disease was changed by the test medicines. The area measurement was conducted using an image measurement software (LAS 3.8, Leica Microsystem Framework, USA), followed by comparison with a control group. The incised liver tissues were fixed with 10% neutral formalin, followed by general tissue treatment procedures. The paraffin-embedded tissues were sliced into a thickness of 4 µm, and then stained with hematoxylin and eosin, followed by microscopic observation.

Statistical Evaluation

All results were expressed as means and standard deviation, and statistical analysis of the obtained data was conducted using the multiple comparison test. The Bartlett's test was used to verify homogeneity across means of samples. If the homogeneity was present, the Dunett's multiple comparison test was conducted to verify whether or not there are differences between the vehicle control groups and the administered groups. If the homogeneity was not recognized as a result of the Bartlett's test, the Kruskal-Wallis test, which is a nonparametric method using ranking data, was conducted, and the Dunett's test was used to investigate the significant difference between groups for p<0.05. This analysis was conducted using a statistical program GraphPad InStat (version 3.05, GraphPad Software Inc.). The hazard rates were set to 5% and 1%.

Results

Histopathological Observation of Atherosclerotic Plaque Formed in Aortic Arch

Figure 2:
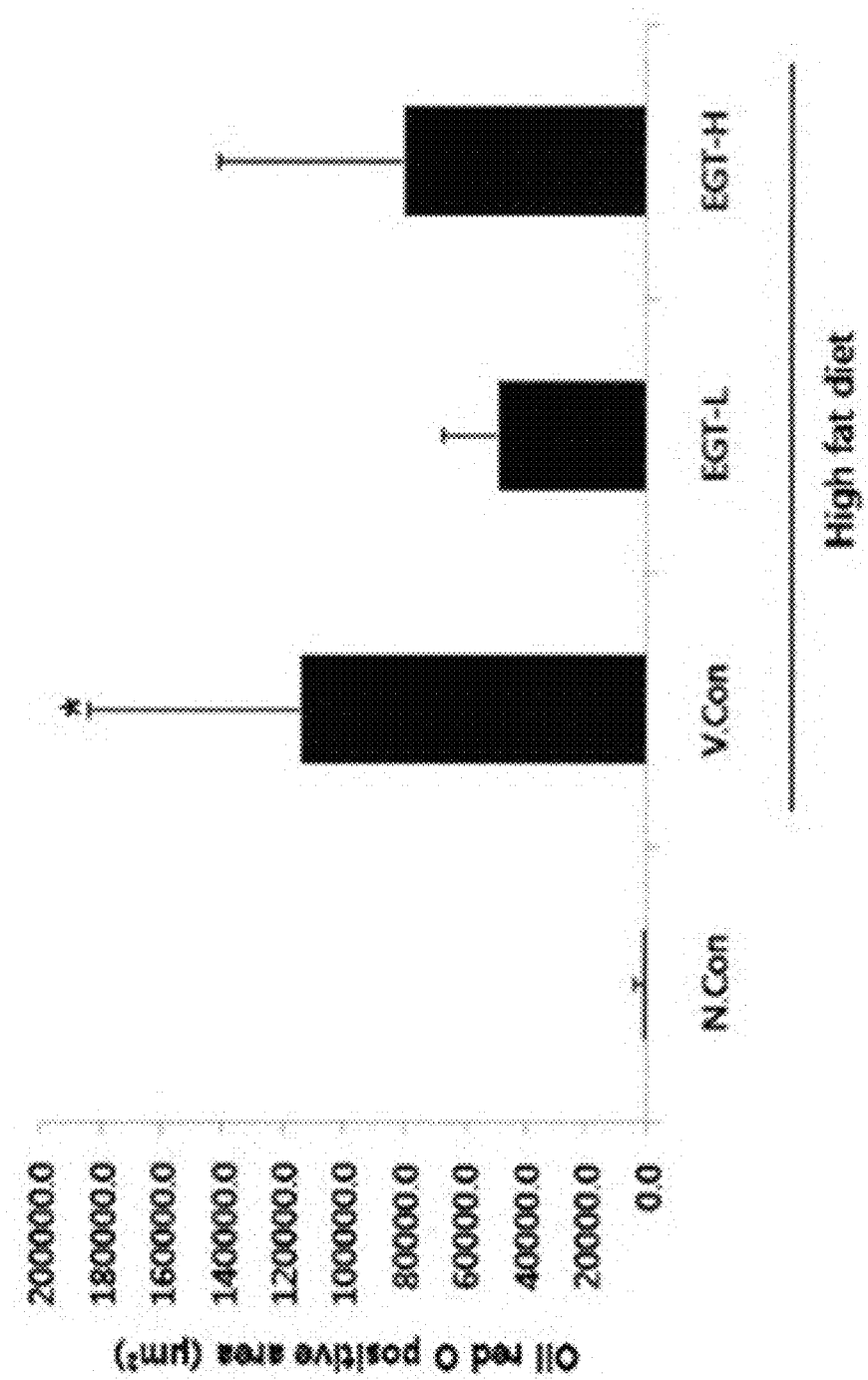
FIG. 2 illustrates images showing quantitative analysis results of atherosclerotic plaque area change according to administration of a protein consisting of the amino acid sequence of SEQ ID NO: 1 in ApoE-KO mice.

In order to evaluate the effect of a protein consisting of the amino acid sequence of SEQ ID NO: 1 on atherosclerosis which was induced by feeding a high-cholesterol diet to ApoE-KO mice for 12 weeks, the aortic arch was stained with Oil Red O. As a result, no lesions were observed in the blood vessel of the normal control group, but the formation of atherosclerotic plaque, which was stained with Oil Red O due to precipitation of the vascular endothelium, was clearly observed in the control group fed with a high-cholesterol diet (V.Con). Whereas, it was observed that the administration of a protein consisting of the amino acid sequence of SEQ ID NO: 1, as a test material, remarkably reduced the formation of atherosclerotic plaque, when compared with the control group. It was observed that the thickness and area of atherosclerotic plaque were significantly reduced in EGT-L group administered with 10 µg/kg protein consisting of the amino acid sequence of SEQ ID NO: 1 and an EGT-H group administered with 10 µg/kg protein consisting of the amino acid sequence of SEQ ID NO: 1 when compared with the control group (FIG. 1). Analysis results of the area of the atherosclerotic plaque using an image analysis program also showed that the formation of atherosclerotic plaque was reduced by about 57% in the EGT-L group compared with the control group, and the lesions were reduced by about 30% in the EGT-H group compared with the control group (FIG. 2).

Histopathological Observation of Liver and Heart for Evaluating Stability on Administration of Protein Consisting of Amino Acid Sequence of SEQ ID NO: 1

Figure 3:
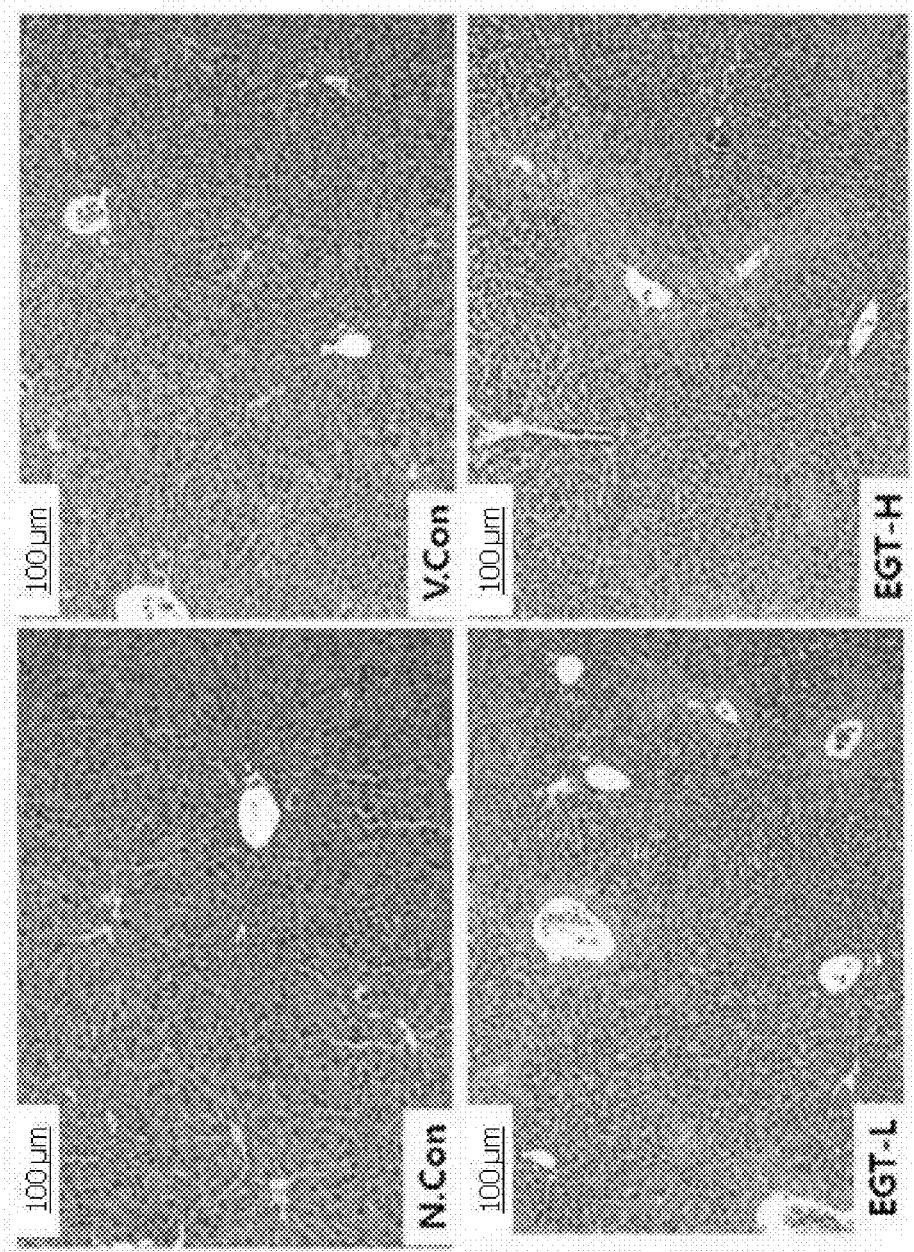
FIG. 3 illustrates images showing pathological analysis results of the liver tissue according to administration of a protein consisting of the amino acid sequence of SEQ ID NO: 1 in ApoE-KO mice.

As a result of evaluation of toxicity and stability of the protein consisting of the amino acid sequence of SEQ ID NO: 1, the histopathological observation of the liver and the kidney showed that light degeneration of fat occurred around the central vein in the control group fed with a high-cholesterol diet (microvacoular change). However, it was observed that the administration of the protein consisting of the amino acid sequence of SEQ ID NO: 1 as a test material did not induce any toxicity (FIG. 3) in the liver, and the kidney was observed to be normal in all test groups (FIG. 4).

Conclusion

As a result of evaluating the effect on arteriosclerosis of the ApoE-KO, which is induced by a high-cholesterol diet, by the administration of the protein consisting of the amino acid sequence of SEQ ID NO: 1, it was observed that the atherosclerotic plaque lesion was remarkably reduced in both of the 10 µg/kg (low concentration)-administered group (EGT-L) and 100 µg/kg (high concentration)-administered group (EGT-H). It was observed that the atherosclerotic plaque lesion was reduced by about 57% in the EGT-L administered group and about 30% in the EGT-H administered group, and it was confirmed that the administration of the protein consisting of the amino acid sequence of SEQ ID NO: 1 suppressed the formation of atherosclerotic plaque when compared with the control group. Meanwhile, it was observed that the administration of both high-concentration and low-concentration proteins consisting of the amino acid sequence of SEQ ID NO: 1 did not show any toxicity in organs, such as the liver and the kidney.

Having described a preferred embodiment of the present invention, it is to be understood that variants and modifications thereof falling within the spirit of the invention may become apparent to those skilled in this art, and the scope of this invention is to be determined by appended claims and their equivalents.

References

Nakashima, Y., A. S. Plump, et al. "ApoE-deficient mice develop lesions of all phases of atherosclerosis throughout the arterial tree." *Arterioscler Thromb* 1994. 14(1): 133-40.

Weiss, D., J. J. Kools, et al. "Angiotensin II-induced hypertension acceleratesthe development of atherosclerosis in apoE-deficient mice." *Circulation* 2001.103(3): 448-54.

Kolovou, G., K. Anagnostopoulou, et al. "Apolipoprotein E knockout models." *Curr Pharm Des* 2008. 14(4): 338-51.

Yamakawa, T., K. Ogihara, et al. "Effect of dehydroepiandrosterone on atherosclerosis in apolipoprotein E-deficient mice." *J Atheroscler Thromb* 2009. 16(4): 501-8.

Amar, M. J., W. D'Souza, et al. "5A apolipoprotein mimetic peptide promotes cholesterol efflux and reduces atherosclerosis in mice." *J Pharmacol Exp Ther* 2010. 334(2): 634-41.

Inanaga, K., T. Ichiki, et al. "Acetylcholinesterase inhibitors attenuate atherogenesis in apolipoprotein E-knockout mice." *Atherosclerosis* 2010. 213(1): 52-8.

What is claimed is:

1. A method for treating atherosclerosis in a subject in need thereof, the method comprising administering to the subject a composition comprising (a) a pharmaceutically effective amount of a protein consisting of the amino acid sequence of SEQ ID NO:1; and (b) a pharmaceutically acceptable carrier.

2. The method of clam 1, wherein the atherosclerosis is one occurred in a patient having a defective apolipoprotein E gene.

* * * * *

SEQUENCE LISTING

<160> NUMBER OF SEQ ID NOS: 1

<210> SEQ ID NO 1
<211> LENGTH: 58
<212> TYPE: PRT
<213> ORGANISM: Artificial Sequence
<220> FEATURE:
<223> OTHER INFORMATION: EGT022 peptide

<400> SEQUENCE: 1

Thr Cys Gln Leu Arg Pro Gly Ala Gln Cys Ala Ser Asp Gly Pro Cys
1               5                   10                  15

Cys Gln Asn Cys Gln Leu Arg Pro Ser Gly Trp Gln Cys Arg Pro Thr
            20                  25                  30

Arg Gly Asp Cys Asp Leu Pro Glu Phe Cys Pro Gly Asp Ser Ser Gln
        35                  40                  45

```
Cys Pro Pro Asp Val Ser Leu Gly Asp Gly
    50                  55
```